United States Patent [19]

Hinck et al.

[11] Patent Number: 6,087,326
[45] Date of Patent: Jul. 11, 2000

[54] NEUROLOGICAL DRUG SCREENS

[75] Inventors: Lindsay Hinck; Kasuko Masu; Masayuki Masu; David Leonardo, all of San Francisco; Marc Tessier-Lavigne, San Mateo, all of Calif.

[73] Assignee: The Regents of the University of California, Oakland, Calif.

[21] Appl. No.: 09/007,604

[22] Filed: Jan. 15, 1998

Related U.S. Application Data

[62] Division of application No. 08/551,874, Oct. 16, 1995, Pat. No. 5,747,262.

[51] Int. Cl.[7] ............................ A61K 38/02; A61K 38/17; C07K 2/00; C07K 14/435
[52] U.S. Cl. ............................... 514/2; 435/7.1; 435/7.2; 435/7.21; 514/12; 530/350
[58] Field of Search .............................. 530/350; 435/7.1, 435/7.2, 7.21; 514/2, 12

[56] References Cited

PUBLICATIONS

Serafini et al., *Cell*, vol. 78, pp. 409–424, 1994.
Vielmetter et al., *J. Cell Bio.*, vol. 127, pp. 2009–2020, 1994.

*Primary Examiner*—Gary L. Kunz
*Assistant Examiner*—Stephen Gucker
*Attorney, Agent, or Firm*—Richard Aron Osman

[57] ABSTRACT

Compositions for identifying lead compounds for pharmacological agents useful in the diagnosis or treatment of neurological disease or injury include mixtures comprising an isolated netrin and an isolated natural netrin receptor such as "Deleted in Colorectal Carcinoma" (DCC) and neogenin. The general methods involve incubating a mixture of an isolated mammalian netrin, an isolated natural mammalian netrin receptor, and a candidate pharmacological agent, and determining if the presence of the agent modulates the binding of the netrin to the receptor.

6 Claims, No Drawings

NEUROLOGICAL DRUG SCREENS

RELATED APPLICATION

This application is a division of Ser. No. 08/551,874 filed Oct. 16, 1996, issued as U.S. Pat. No. 5,747,262 on May 5, 1998.

The research carried out in the subject application was supported in part by grants from the National Institutes of Health. The government may have rights in any patent issuing on this application.

INTRODUCTION

1. Field

The field of the invention is neurological drug screening using mammalian netrins and natural mammalian netrin receptors.

2. Background

The netrins are a family of proteins that are profound modulators of growth of developing axons, functioning as attractants for some axons and repellents of other axons. As such, the modulation of these effects provides an important therapeutic pathway for assisting the regeneration of axons in adult nervous system (e.g. following injury or trauma).

The ability to construct high-throughput pharmaceutical screens for modulators of netrin activity has been limited by the lack of identifiable mammalian netrin receptors. Identifying receptors on axons that mediate neural responsiveness to netrins will provide key targets for identifying lead pharmaceuticals for therapeutic intervention in the nervous system.

Relevant Literature

Ishii et al. (1992) Neuron 9, 873–881, describe unc-6, a nematode gene with sequence similarity to mammalian netrin genes. Leung-Hagenstein et al. (1992) Cell 71, 289–299, Hedgecock et al. (1990) Neuron 2, 61–85 and Hamelin et al. (1993) Nature 364, 327–330, describe two other genes, unc-5 and unc-40 that are in the same genetic pathway as unc-6 and have sequence similarity to the vertebrate genes, "Deleted in Colorectal Carcinoma" (DCC) and neogenin (Fearon et al. (1990) Science 247, 49–56, Hendrick et al. (1994), and Vielmetter et al. (1994) JCB 127, 2009–2020). Cho et al. (1995) Current Opinion in Genetics and Development 5, 72–78, provide a recent review of DCC function. See also: Colamarino & Tessier-Lavigne (1995) Cell 81, 621–629; Kennedy et al. (1994) Cell 78, 425–435; and Serafini et al. (1994) Cell 71, 289–299.

SUMMARY OF THE INVENTION

The invention provides methods and compositions for identifying lead compounds for pharmacological agents useful in the diagnosis or treatment of neurological disease or injury. In particular, the invention provides mixtures comprising an isolated netrin and an isolated natural netrin receptor capable of specifically binding said netrin. Exemplary netrin receptors-include DCC and neogenin. The general methods involve incubating a mixture comprising an isolated netrin, an isolated natural netrin receptor, and a candidate pharmacological agent, and determining if the presence of the agent modulates the binding of the netrin to the receptor. Specific agents provide lead compounds for pharmacological agents useful in the diagnosis or treatment of neurological disease or injury.

DETAILED DESCRIPTION

The invention provides methods and compositions for identifying lead compounds for pharmacological agents useful in the diagnosis or treatment of mammalian, particularly human, neurological disease or injury. The methods rely on monitoring the interaction of a mammalian, particularly human, netrin and a corresponding netrin receptor in the presence and absence of a candidate agent. A wide variety of assays can be used, including receptor activation assays and binding assays. Binding assays may monitor netrin binding to the extracellular domain of a full-length receptor expressed on a cell, or in vitro protein-protein binding of a netrin to a C-terminal truncated receptor. Typically, such in vitro screens involve the immobilization of one of the binding partners on a solid substrate.

Invariably, the assays involve a mixture comprising an isolated netrin and an isolated natural netrin receptor capable of specifically binding said netrin. Exemplary netrin receptors used in the assays include DCC and neogenin. We have demonstrated that these mammalian gene products function as natural mammalian, and in particular, human, netrin receptors. The general methods comprise steps: forming a mixture comprising an isolated netrin, an isolated natural netrin receptor, and a candidate pharmacological agent; incubating said mixture under conditions whereby, but for the presence of said candidate pharmacological agent, said netrin specifically binds said netrin receptor at a first binding affinity; and detecting a second binding affinity of said netrin to said netrin receptor, wherein a difference between said first and second binding affinity indicates that said candidate pharmacological agent is a lead compound for a pharmacological agent useful in the diagnosis or treatment of neurological disease or injury.

The following examplary assay is offered by way of illustration and not by way of limitation: Ligand Screening of Transfected COS cells.

I. Prepare the Ligand

Expression Construct: cDNA encoding the targeted netrin is tagged with the Fc—portion of human IgG and subcloned into a 293 expression vector (pCEP4: In Vitrogen).

Transfection: 293 EBNA cells are transfected ($CaPO_4$ method) with the netrin expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco) and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Prepare Truncated Receptor (Positive Control)

Expression Construct: cDNA encoding a corresponding netrin receptor deletion mutant comprising the extracellular domain (truncated immediately N-terminal to the transmembrane region) is subcloned into a 293 expression vector (pCEP4: In Vitrogen).

Transfection: 293 EBNA cells are transfected ($CaPO_4$ method) with the receptor mutant expression construct. After 24 h recovery, transfected cells are selected with G418 (geneticin, 250 ug/ml, Gibco) and hygromycin (200 ug/ml). Once the selection process is complete, cells are maintained in Dulbecco's Modified Eagles medium (DME)/10% FCS under selection.

Preparation of Conditioned Medium: Serum-containing media is replaced with Optimem with glutamax-1 (Gibco)

and 300 ng/ml heparin (Sigma), and the cells are conditioned for 3 days. The media is collected and spun at 3,000×g for 10 minutes. The supernatant is filtered (0.45 um) and stored with 0.1% azide at 4° C. for no more than 2 weeks.

II. Transfect COS Cells

Seed COS cells (250,000) on 35 mm dishes in 2 ml DME/10% FCS. 18–24 h later, dilute 1 ug of netrin receptor-encoding DNA (cDNA cloned into pMT21 expression vector) into 200 ul serum-free media and add 6 ul of Lipofectamine (Gibco). Incubate this solution at room temperature for 15–45 min.

Wash the cells 2X with PBS. Add 800 ul serum-free media to the tube containing the lipid-DNA complexes. Overlay this solution onto the washed cells.

Incubate for 6 h. Stop the reaction by adding 1 ml DMA/20% FCS. Refeed cells. Assay cells 12 hr later.

III. Ligand Binding Assay

Wash plates of transfected COS cells 1X with cold PBS (plus Ca/Mg)/1% goat serum. Add 1 ml conditioned media neat and incubate 90 min at room temp.

Wash plates 3X with PBS (plus Ca/Mg). On the 4th wash, add 1 ml 50% methanol to 1 ml PBS. Then add 1 ml methanol. Evacuate and add 1 ml methanol.

Wash 1X with PBS. Wash 1X PBS/1% goat serum.

Add secondary antibody (1-to-2,000 anti-human Fc conjugated to alkaline phosphatase (Jackson Lab)) in PBS/1% goat serum. Incubate 30–40 min room temp.

Wash 3X with PBS. Wash 1X alkaline phosphatase buffer (100 mM Tris-Cl, pH 9.5, 100 mM NaCl, 5 mM MgCl). Prepare alkaline phosphatase reagents: 4.5 ul/ml NBT and 3.5 ul/ml BCIP (Gibco) in alkaline phosphatase buffer.

Incubate 10–30 min, quench with 20 mM EDTA in PBS. Cells that have bound netrin are visible by the presence of a dark purple reaction product.

In parallel incubations, positive controls are provided by titrating netrin binding with serial dilutions of the mutant receptor conditioned medium.

IV. Results: Binding of Netrin to Netrin Receptor

Cell expressing mammalian netrin were shown to bind netrin receptor. No reactivity was observed with control COS cells or with receptor-expressing COS cells in the presence of the secondary antibody but in the absence of the netrin-Fc fusion. Binding was observed to receptor-expression cells using a construct in which netrin is fused directly to alkaline phosphatase, for which a secondary antibody is not required. Receptor deletion mutants titrate the netrin-receptor binding, serving as a positive control for inhibition assays.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A mixture comprising an isolated mammalian netrin and an isolated mammalian netrin receptor selected from the group consisting of "Deleted in Colorectal Carcinoma" (DCC) and neogenin.

2. A mixture according to claim 1, wherein said receptor is "Deleted in Colorectal Carcinoma" (DCC).

3. A mixture according to claim 1, wherein said receptor is neogenin.

4. A mixture according to claim 1, wherein said netrin is a human netrin and said receptor is "Deleted in Colorectal Carcinoma" (DCC).

5. A mixture according to claim 1, wherein said netrin is a human netrin and said receptor is neogenin.

6. A mixture according to claim 1, wherein said netrin is a human netrin.

* * * * *